United States Patent
Kawato

(10) Patent No.: US 7,643,267 B2
(45) Date of Patent: Jan. 5, 2010

(54) OPTICAL EMISSION SPECTROMETRY DEVICE

(75) Inventor: Eizo Kawato, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 524 days.

(21) Appl. No.: 11/686,710

(22) Filed: Mar. 15, 2007

(65) Prior Publication Data

US 2008/0224626 A1 Sep. 18, 2008

(51) Int. Cl.
*F23Q 3/00* (2006.01)
*H05B 37/02* (2006.01)

(52) U.S. Cl. .............. 361/257; 361/253; 361/256; 361/247; 361/263; 315/209 CD; 315/209 M; 315/209 T; 315/209 R

(58) Field of Classification Search ........ 361/253, 361/257, 256, 263, 247; 315/209 CD, 209 M, 315/209 T, 209 R, 274, 243
See application file for complete search history.

(56) References Cited

U.S. PATENT DOCUMENTS

| | | | | |
|---|---|---|---|---|
| 3,731,183 A | * | 5/1973 | Johnson et al. | 323/237 |
| 3,911,886 A | * | 10/1975 | Nagasawa | 123/603 |
| 5,777,867 A | * | 7/1998 | Hongu et al. | 363/134 |
| 6,156,999 A | * | 12/2000 | Ignatchenko et al. | 219/130.4 |
| 6,564,786 B2 | * | 5/2003 | Kameda et al. | 123/606 |
| 7,095,181 B2 | * | 8/2006 | Frus et al. | 315/209 CD |

* cited by examiner

Primary Examiner—Tuyet Vo
(74) Attorney, Agent, or Firm—J.C. Patents

(57) ABSTRACT

An optical emission spectrometry device is provided. In the optical emission spectrometry device, a discharge path is formed by connecting an ignition circuit to a discharge gap, and further connecting in parallel a plurality of sets of coils and driving circuits, each set having one coil and one driving circuit. Each driving circuit has two operation modes: an increasing operation mode of applying a predetermined potential difference to the corresponding coil of the set to increase the current passing through the corresponding coil, and a sustaining operation mode of directly connecting the corresponding coil of the set to the discharge path to sustain the current passing through the corresponding coil. Moreover, each driving circuit is controlled in such a way that the timing for the increasing operation mode in which the current passing through the coil increases alternates with the timing for the increasing operation mode of other driving circuit.

10 Claims, 3 Drawing Sheets

OPTICAL EMISSION SPECTROMETRY DEVICE

BACKGROUND OF THE INVENTION

1. Field of the Invention

The present invention relates to an optical emission spectrometry device in which the constituting atoms of a sample are evaporated to emit light through discharge and the optical intensity is measured for analyzing the elementary composition of the sample. More particularly, the present invention relates to an optical emission spectrometry device in which a high-current spark discharge is generated between a metal sample and a discharge electrode, and a plurality of elements is analyzed simultaneously in a short time.

2. Description of Related Art

A spark discharge is generated by an optical emission spectrometry device between a metal sample and a discharge electrode (a discharge gap). Through a high-current discharge, the atoms on the surface of the metal sample are evaporated, and the evaporated atoms are excited by discharge plasma. As the excited atoms emit light with a line spectrum inherent in the respective elements, the amount of the elements existing in the plasma is obtained by introducing the light into a spectrometer to measure the intensity of the light of a specific wavelength. Therefore, through simultaneous measurements on lights of a plurality of wavelengths, the amount of each element in the plasma is determined. Based on the resulting information, the elementary composition of the metal sample is derived.

In an optical emission spectrometry device in the prior art, a capacitor charged with several hundreds of volts is connected in advance between a metal sample and an electrode (a discharge gap), and discharge is commenced by an ignition circuit 12 (12a-12d). The ignition circuit may be connected in series to a discharge path formed by the discharge gap with a coil 13 and a capacitor 14, as shown in FIGS. 1A and 1C, or may be connected in parallel to the above discharge path, as shown in FIGS. 1B and 1D. Upon the beginning of the discharge, the energy stored in the capacitor 14 increases the discharge current rapidly, and creates a high-energy spark discharge between a metal sample 32 and a discharge electrode 31. In the mean time, the temperature on the surface of the metal sample 32 is significantly elevated, such that the atoms constituting the sample begin to be evaporated. The coil 13 is connected to limit the discharge current. Additionally, a recharge circuit 15 is also disposed for recharging the capacitor 14, which has lost energy due to the discharge.

The evaporated atoms are excited by electrons in the plasma. Afterward, when resuming a stable state, the excited atoms emit a light with a wavelength corresponding to the energy difference. As each element has its inherent energy levels, the wavelengths of the light also form an inherent line spectrum of the elements. The emitted light in the plasma is efficiently introduced to the spectrometer, and the optical intensity indicative of each of the plurality of elements is simultaneously measured. The optical intensity of each wavelength is not simply proportional to the elementary composition, but is roughly proportional to the amount of each element, the elementary composition can be determined by computing the relationship between the optical intensity and the amount of the elements in advance and converting the optical intensity into the amount of the elements.

In order to prevent changes in the surface condition of the sample during the analysis, an inert gas, etc., is usually filled the space between the metal sample 32 and the discharge electrode 31. As the metal sample and the discharge electrode 31 are arranged with a space, i.e. a discharge gap, of about several millimeters, the discharge may not start by applying a voltage of several hundreds of volts. Therefore, the ignition circuit 12 is disposed to generate a high voltage in the discharge gap to initiate the discharge. The ignition circuit 12 may utilize the voltage boosting function of a transformer, as shown in FIGS. 1A and 1B, or utilize the electromotive force generated by breaking the current, as shown in FIGS. 1C and 1D, and so on. For example, a voltage of several hundreds of volts is applied to the primary circuit in the transformer, such that a high voltage of several kV to tens of kV is generated on the secondary circuit and applied to the discharge gap. Alternatively, a voltage of tens of volts is continually applied to the primary circuit at a fixed period of time. When the current turns into several amperes to tens of amperes, voltage that is being applied to the primary circuit ceases, such that an induced electromotive force is generated and a high voltage of several kV to tens of kV is generated on the secondary circuit. However, the primary circuit and the secondary circuit are not necessarily separated and can be interconnected. Alternatively, a coil may be excited to generate an induced electromotive force.

If a high voltage is generated in the discharge gap 11 by the ignition circuit 12, a discharging occurs in the gap and the discharge current flows in the gap, while the voltage in the gap decreases rapidly. If the capacitor 14 charged with several hundreds of volts is connected to the discharge gap 11, energy is supplied by the capacitor 14 to produce high-current plasma. However, as the impedance of the plasma decreases with the increase of the current, an excessively high current will occur if the capacitor 14 is directly connected to the discharge gap, such that the plasma cannot be maintained for a fixed period of time. Therefore, a coil 13 is usually connected between the capacitor 14 and the discharge gap 11 for controlling the increasing rate of the current and maintaining an appropriate current value. Through appropriate selections of the capacitance and charging voltage for the capacitor 14 and the inductance for the coil 13, a proper current waveform of several tens of amperes to several hundreds of amperes may be selected. Alternatively, as shown in FIG. 2, a more complicated current waveform can be synthesized by preparing in advance several series circuits of capacitors 14 and the coils 13 and connecting them in a proper combination circuit based on the application. In FIG. 2, same or like components are designated with identical reference numbers as in FIGS. 1A~1D. In the figure, an ignition circuit is depicted by reference numeral 22, the coils are depicted by the reference numerals 23a-23c, the capacitors are depicted by the reference numerals 24a-24c, the recharge circuits are depicted by the reference numerals 25a-25c, and the discharge path switch elements are depicted by the reference numerals 27a-27c. In alteration, the combination of mechanical elements such as relays or semiconductor elements such as metal oxide semiconductor field effect transistors (MOSFETs) or thyristors, can be used. In addition, all of the recharge circuits may share a common power supply.

As such, the current waveform may be selected through the combination of capacitors and coils. However, as the resulting current waveform is determined by the combination of capacitors and coils, the current value cannot be selected optionally. Moreover, as the discharge ends due to the loss of the energy charged to the capacitor, the time duration of the discharge cannot be controlled unrestrictedly.

Therefore, in order to control the discharge current at an arbitrary value, a driving circuit 16, for example, as shown in FIG. 3 is used. Initially, a capacitor with sufficiently increased capacitance, which continually supplies a current to the discharge gap, or a power supply 34 is prepared. After that, a switch element 33 for switching the connection is disposed to connect the coil 13 to the capacitor or the power supply, or directly connect the coil 13 to the discharge path (ground). The capacitor is provided with a circuit for recharging. By using the driving circuit 16 consisting of the capacitor or the power supply 34 and the switch element 33, the value of the discharge current can be arbitrarily controlled. Such an approach is usually referred to as a forward converter in the field of power supply circuits. When the current value is smaller than a target value, the current through the coil increases after the coil is connected to the capacitor or power supply. When the current value exceeds the target value, the current through the coil is sustained with the electromagnetic energy stored in the coil after the coil is grounded. As the switch element must have a high switching speed of a certain degree, semiconductors such as MOSFETs shown in FIGS. 4A and 4B are often used. In FIG. 4A, components 35 and 36 are MOSFETs, and component 37 is a MOSFET control circuit. However, a diode 38 may be used as the element grounded as shown in FIG. 4B for simplicity.

In the conventional optical emission spectrometry device, the current waveform may be controlled through a forward converter approach. However, as the current increases when the coil is connected to the power supply and the current decreases when the coil is disconnected from the power supply, the current waveform is formed like a saw-tooth shape. Therefore, the optical intensity also oscillates in a saw-tooth shape, which impairs the spectrometry precision or reproducibility. By shortening the interval between driving circuit switches, variation in the current value may be reduced; however, as the switching loss of the switch element in the driving circuit is further increased, the problem of reducing energy transfer efficiency may occur.

SUMMARY OF THE INVENTION

Accordingly, the present invention is directed to provide an optical emission spectrometry device in which a discharge path is formed by connecting an ignition circuit to a discharge gap, and further connecting in parallel a plurality of sets of coils and driving circuits, each set having one coil and one driving circuit. The present invention is characterized in that each of the driving circuits have two operation modes: an increasing operation mode of applying a predetermined potential difference to the corresponding coil of the set to increase the current passing through the corresponding coil, and a sustaining operation mode of directly connecting the corresponding coil of the set to the discharge path to sustain the current passing through the corresponding coil. Moreover, each of the driving circuits is controlled in such a way that the timing for the increasing operation mode in which the current through the coil increases alternates with the timing for the increasing operation mode of other driving circuit.

In addition, a method of controlling the optical emission spectrometry device is provided, wherein a discharge path is formed by connecting an ignition circuit to a discharge gap and further connecting in parallel a plurality of sets of coils and driving circuits, each set having one coil and one driving circuit. Moreover, each of the driving circuits has two operation modes: an increasing operation mode of applying a predetermined potential difference to the corresponding coil of the set to increase the current passing through the corresponding coil, and a sustaining operation mode of directly connecting the corresponding coil of the set to the discharge path to sustain the current passing through the corresponding coil. The method is characterized in that each of the driving circuits is controlled in such a way that the timing for the increasing operation mode in which the current through the coil increases alternates with the timing for the increasing operation mode of other driving circuit.

In the optical emission spectrometry device provided by the present invention, as the discharge current is dispersed into a plurality of coils and driving circuits, the magnitude of the current controlled by each element is reduced and meanwhile the switching frequency of each element is reduced, such that the switching loss of the switches in the driving circuits is reduced and the energy transfer efficiency is improved.

Alternatively, as the variation in the discharge current reduces when the energy transfer efficiency remains fixed, the variation in the optical intensity is reduced compared with the optical emission spectrometry device in the prior art, and thus, the spectrometry precision or reproducibility are improved.

DESCRIPTION OF EMBODIMENTS

An optical emission spectrometry device provided by the present invention is described in details below with reference to the drawings.

Figure 1A:
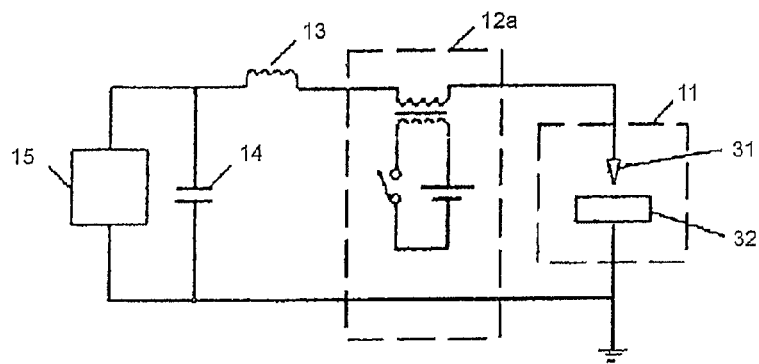
FIGS. 1A~1D are schematic diagrams of discharge circuits in the prior art.
Figure 1B:
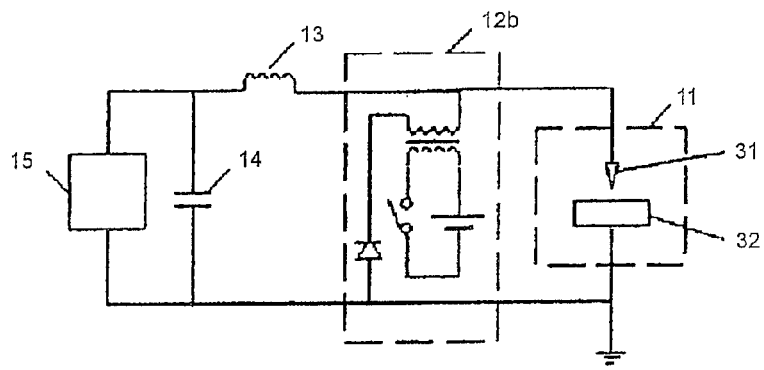
Figure 1C:
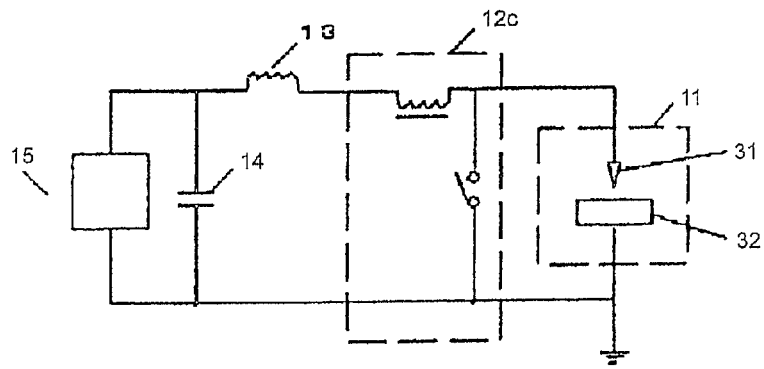
Figure 1D:
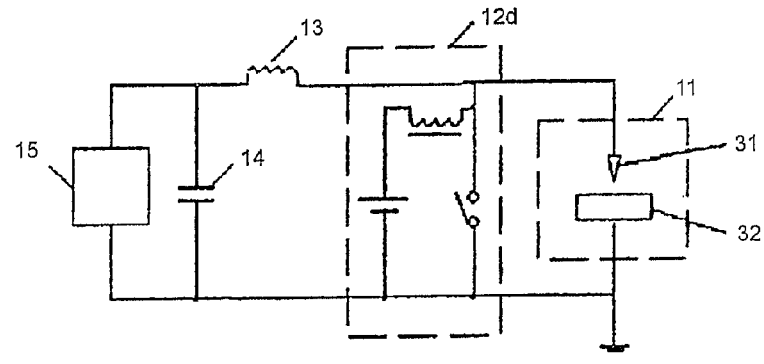
Figure 2:
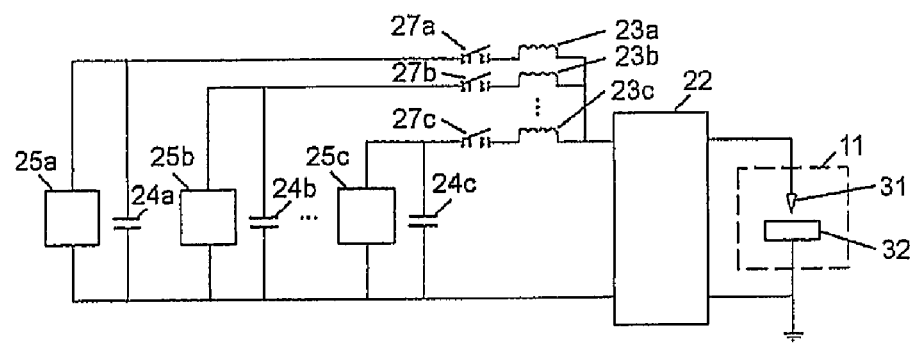
FIG. 2 is a schematic diagram of a control circuit for the discharge current in the prior art.
Figure 3:
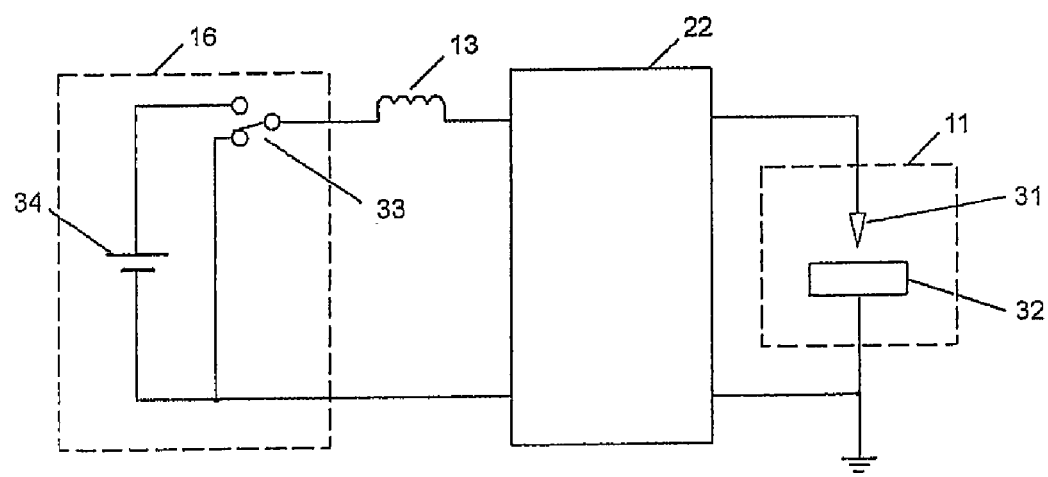
FIG. 3 is a discharge circuit adopting a forward converting approach.
Figure 4A:
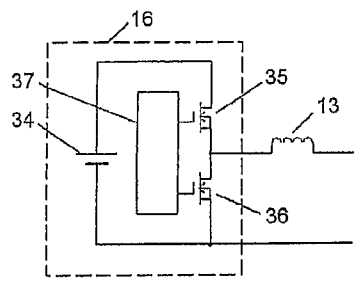
FIGS. 4A, 4B are examples of driving circuits for forward converters.
Figure 4B:
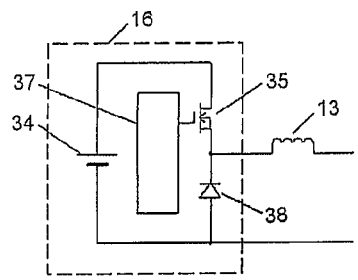
Figure 5:
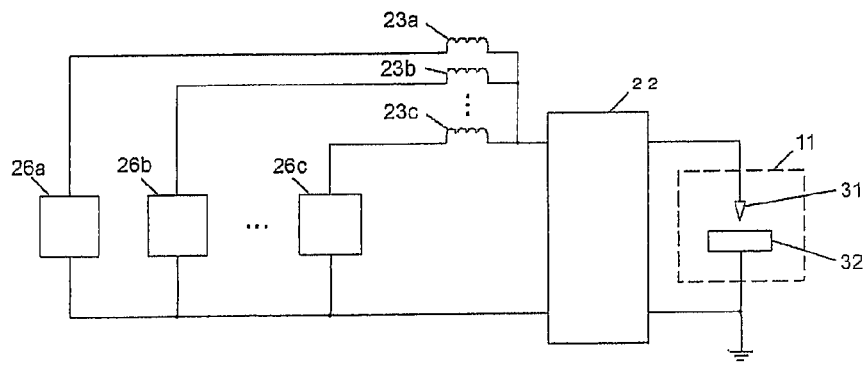
FIG. 5 is a schematic diagram of a control circuit for a discharge current in an optical emission spectrometry device according to an embodiment of the present invention.

FIG. 5 shows an example of a discharge circuit of an optical emission spectrometry device, in which the same or like components are designated with identical reference numbers in FIGS. 1 to 3. Initially, as in the optical emission spectrometry device in the prior art, an ignition circuit 22 starts discharge in the discharge gap 11. Upon discharge, several driving circuits 26a-26c are sustained in a state in which the current through the coils increases. Such a state of the driving circuits is simply known as an "ON" state. As such, a high-energy spark discharge is created between a metal sample 32 and a discharge electrode 31 (a discharge gap). If the discharge current reaches a preset specific upper limit value, the control current maintained at the "ON" state is switched to a state in which the current through the coils is sustained, and such a state of the driving circuit is simply known as an "OFF" state. In another aspect, if the discharge current reaches a preset lower limit value, the control current maintained at the "OFF" state is switched to the "ON" state. As such, when the state of the driving circuits 26a-26c connected to the discharge path is switched, selection and switching are done sequentially for all the connected driving circuits. Additionally, when the upper limit for the current value is reached and when the current value continues to increase after one driving circuit is switched to the "OFF" state, the operation is further repeated to switch the other driving circuits to the "OFF" state. On the contrary, when the lower limit for the current value is reached and when the current value continues to decrease after one driving circuit is switched to the "ON" state, the operation is further repeated to switch the other driving circuits to the "ON" state.

Figure 6:
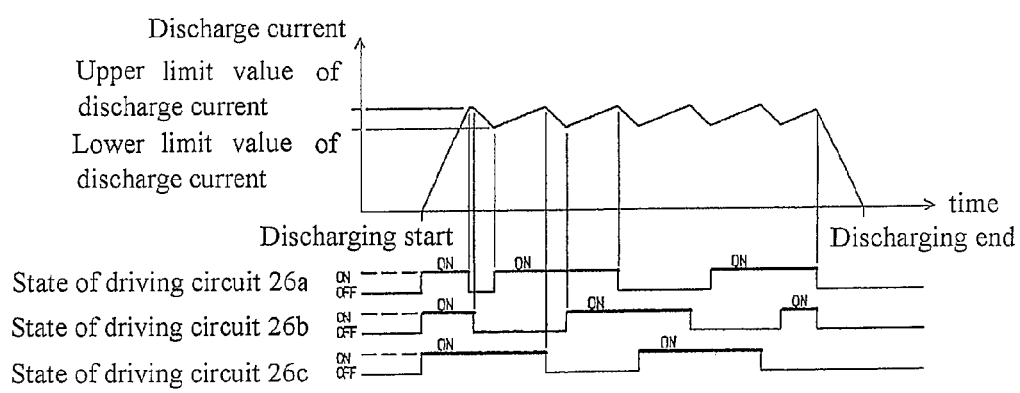
FIG. 6 is a diagram illustrating a method of controlling a discharge current using an optical emission spectrometry device according to an embodiment of the present invention.

In FIG. 6, using an optical emission spectrometry device having three driving circuits 26a, 26b, and 26c as an illustrative example, the various situations of the operation modes of each driving circuit and of the discharge current are shown. Shortly after the ignition circuit starts discharging, the three driving circuits 26a-26c are all maintained in the "ON" state. When the discharge current reaches an upper limit value, the driving circuit 26a is switched to the "OFF" state. At this point, as the driving circuits 26b and 26c are at the "ON" state, the state in which the discharge current increases, the driving circuit 26b is further switched to the "OFF" state. Only when the driving circuit 26c is at the "ON" state, the discharge current is reduced. When the discharge current is reduced and reaches the lower limit value, the driving circuit 26a, which has previously been switched to the "OFF" state, is switched to the "ON" state. When the discharge current increases and reaches the upper limit value again, the driving circuit 26c is switched to the "OFF" state. By repeating the above action, the current value oscillates between the upper limit value and lower limit value preset for the discharge current. After a specific discharge time, the discharging ends if the driving circuits 26a-26c are all switched to the "OFF" state.

In the above embodiment, upon starting discharge, all three driving circuits 26a-26c are at the "ON" state. However, in order to obtain the required increasing rate of the current, the number of the driving circuits at the "ON" state may vary on demands. Besides, if the state of each of the driving circuits 26a-26c before starting discharge caused by the ignition circuit 22 is the state permitted by the actual device, the state can be either the "ON" or the "OFF" state.

Although the control through a fixed upper limit value and lower limit value has been provided herein, it is appreciated that by varying the upper limit value and the lower limit value over time, an arbitrary waveform of the discharge current can be generated.

In addition, although the circumstance of three driving circuits has been disclosed, it is appreciated that by increasing the number of sets of coils and driving circuits, the current value can be controlled in greater detail.

In the above description, under the precondition that all of the driving circuits have an identical supply voltage and identical coil inductance, driving circuits with different coil inductances or different supply voltages can be further connected in parallel in order to generate a non-periodic and non-sustained discharge current. For example, when the increasing rate of the discharge current is increased to form a high-current plasma shortly after the discharge begins, it is effective that not only a plurality of discharge circuits is placed at the "ON" state, but also a circuit with a higher supply voltage and a lower coil inductance is additionally disposed and switched to the "ON" state, such that the current value increases rapidly. It is necessary to connect a diode to the coil to prevent a reverse flow.

In the above example of the circuit, a snubber circuit and the like for absorbing unnecessary induced electromotive forces are omitted. However, capacitors, diodes, and resistors, etc., can be connected on demands. In addition, a control circuit and the like for switching the driving circuit between the "ON" state and the "OFF" state are also omitted, and proper control circuits can certainly be added.

In addition, the portions not shown in the drawings are identical to those in the conventional optical emission spectrometry device. Those portions are used for introducing the light emitted from the discharge gap to the spectrometer, detecting a light with an appropriate wavelength, and collecting and analyzing data, etc.

Compared with the example of the present invention having three driving circuits as described above, the discharge circuit utilizing the forward converter approach in the prior art is equivalent to connecting three coils with 3 times the inductance and driving circuits with ⅓ of the current value in parallel and switching the above three driving circuits simultaneously. At this point, based on the current value when the three driving circuits are all at the "ON" state and the current value when the three driving circuits are all at the "OFF" state, as the variation of the current value is large, the discharge current varies more rapidly between the upper limit value and lower limit value. Therefore, as the switching frequency of the driving circuit increases, the switching loss of the switch element is apparently increased when compared with the present invention; thus, the energy transfer efficiency is reduced.

In view of the above, according to the optical emission spectrometry device of the present invention, as the discharge current is dispersed to a plurality of coils and driving circuits, the magnitude of the current controlled by each element is reduced. In the meantime, the switching frequency of each element is reduced, such that the switching loss of the switch element in the driving circuits is mitigated, and the energy transfer efficiency is improved.

Alternatively, when the energy transfer efficiency remains fixed, as the variation in the discharge current is reduced, the variation in the optical intensity become less when compared with the optical emission spectrometry device in the prior art, and the spectrometry precision or reproducibility are improved.

In addition, it is appreciated that the above embodiment is only an example of the present invention. Various modifications or variations made within the scope of the spirit of the present invention are also covered by the present invention.

What is claimed is:

1. An optical emission spectrometry device, forming a discharge path by connecting an ignition circuit to a discharge gap and further connecting in parallel a plurality of sets of coils and driving circuits, each set having one coil and one driving circuit, wherein:

each driving circuit has two operation modes comprising an increasing operation mode of applying a fixed potential difference to the corresponding coil of the set to increase a current passing through the corresponding coil, and a sustaining operation mode of directly connecting the corresponding coil of the set to the discharge path to sustain the current passing through the corresponding coil, each driving circuit is controlled in such a way that a timing for the increasing operation mode in which the current through the coil increases alternates with a timing for the increasing operation mode of other driving circuit.

2. The optical emission spectrometry device as claimed in claim 1, wherein when a discharge current reaches a preset specific upper limit value, the driving circuits are switched from the increasing operation mode in which the current through the coils increases to the sustaining operation mode in which the current through the coils is sustained.

3. The optical emission spectrometry device as claimed in claim 2, wherein when the discharge current reaches the upper limit value and after one of the driving circuits is switched to the sustaining operation mode in which the current through the corresponding coil of the same set is sustained, and the discharge current continues to increase, the other driving circuits are repeatedly switched to the sustaining operation mode in which the current through the other coils is sustained.

4. The optical emission spectrometry device as claimed in claim 1, wherein when the discharge current reaches a preset specific lower limit value, the driving circuits are switched from the sustaining operation mode in which the current through the coils is sustained to the increasing operation mode in which the current through the coils increases.

5. The optical emission spectrometry device as claimed in claim 4, wherein when the discharge current reaches the lower limit value, and after one of the driving circuits is switched to the increasing operation mode in which the current through the corresponding coil of the same set increases, and the discharge current continues to decrease, the other driving circuits are repeatedly switched to the increasing operation mode in which the current through the other coils increases.

6. A method of controlling the optical emission spectrometry device, forming a discharge path by connecting an ignition circuit to a discharge gap and further connecting in parallel a plurality of sets of coils and driving circuits, each set having one coil and one driving circuit wherein each driving circuit has two operation modes comprising an increasing operation mode of applying a fixed potential difference to the corresponding coil of the set to increase a current passing through the corresponding coil, and a sustaining operation mode of directly connecting the corresponding coil of the set to the discharge path to sustain the current passing through the corresponding coil, wherein each driving circuit is controlled in such a way that a timing for the increasing operation mode in which the current through the coil increases alternates with a timing for the increasing operation mode of other driving circuit.

7. The method of controlling the optical emission spectrometry device as claimed in claim 6, wherein when a discharge current reaches a preset specific upper limit value, the driving circuits are switched from the increasing operation mode in which the current through the coils increases to the sustaining operation mode in which the current through the coils is sustained.

8. The method of controlling the optical emission spectrometry device as claimed in claim 7, wherein when the discharge current reaches the upper limit value and after one of the driving circuits is switched to the sustaining operation mode in which the current through the corresponding coil of the same set is sustained, and the discharge current continues to increase, the other driving circuits are repeatedly switched to the sustaining operation mode in which the current through the other coils is sustained.

9. The method of controlling the optical emission spectrometry device as claimed in claim 6, wherein when the discharge current reaches a preset specific lower limit value, the driving circuits are switched from the sustaining operation mode in which the current through the coils is sustained to the increasing operation mode in which the current through the coils increases.

10. The method of controlling the optical emission spectrometry device as claimed in claim 9, wherein when the discharge current reaches the lower limit value, and after one of the driving circuits is switched to the increasing operation mode in which the current through the corresponding coil of the same set increases, and the discharge current continues to decrease, the other driving circuits are repeatedly switched to the increasing operation mode in which the current through the other coils increases.

* * * * *